United States Patent [19]

Arnold et al.

[11] Patent Number: 5,478,578
[45] Date of Patent: Dec. 26, 1995

[54] POWDERS FOR INHALATION

[75] Inventors: Klaus Arnold; Peter Grass, both of Ingelheim am Rhein; Adolf Knecht, Freiburg; Robert Roos, Ingelheim am Rhein; Gerhard Sluke, Ingelheim am Rhein; Herbet Thieme, Ingelheim am Rhein; Joachim Wenzel, Ingelheim am Rhein, all of Germany

[73] Assignee: Boehringer Ingelheim KG, Ingelheim am Rhein, Germany

[21] Appl. No.: 244,737

[22] PCT Filed: Dec. 12, 1992

[86] PCT No.: PCT/EP92/02814

§ 371 Date: Aug. 15, 1994

§ 102(e) Date: Aug. 15, 1994

[87] PCT Pub. No.: WO93/11746

PCT Pub. Date: Jun. 24, 1993

[30] Foreign Application Priority Data

Dec. 10, 1991 [DE] Germany ............... 41 40 689.3

[51] Int. Cl.⁶ ............... A61K 9/14; A61K 47/26; A61K 47/30; A61K 47/02
[52] U.S. Cl. ............... 424/499; 424/489; 424/500; 424/501; 424/502; 514/951
[58] Field of Search ............... 424/489, 499, 424/500, 501, 502; 514/951

[56] References Cited

U.S. PATENT DOCUMENTS 2,533,065  12/1950  Taplin et al. ............... 424/499
3,957,965   5/1976  Hartley et al. ............... 424/14

Primary Examiner—Nathan M. Nutter
Attorney, Agent, or Firm—R. P. Raymond; M-E. M. Devlin; A. R. Stempel

[57] ABSTRACT

In order to control and optimize the amount of inhalable active substance released when drugs are administered as inhalation powders, the invention calls for the use of auxiliaries consisting of mixtures of coarser particles (average particle size>20 μm) and finer particles (average particle size<10 μm).

8 Claims, No Drawings

POWDERS FOR INHALATION

The invention relates to powders for inhalation consisting of micronised active substance and carriers having specific proportions of finely divided and coarser particles and optimisation or control of the inhalable active substance content of the powders for inhalation.

It is known to improve the properties of powdered inhalable preparations which are important in practice by combining the drug having an effective particle size of about 0.01–10 μm with a water-soluble carrier which has an effective particle size of between 30 and 80 μm (DE-A-1792207).

Excipients are particularly necessary in powders for inhalation if the efficacy of the pharmaceutical substance used is very high, so that only small amounts are needed for each individual dose. In this case it is advisable to dilute the active substance so as to achieve good accuracy of metering.

The usually relatively high proportion of excipient essentially determines the properties of the powder. This is particularly true of the flow characteristics. The finer the powder, the poorer its flow properties, generally speaking. Since good flow properties are the prerequisite for good accuracy of metering when filling individual containers with a prepared dose, eg. when preparing capsules for powder inhalation in conventional capsule machines, the excipient used must not be too fine.

Apart from the effect on the accuracy of metering, the particle size of the excipient is of major importance to the emptying characteristics of capsules when they are used in an inhaler. It has been found that the inhalable, active substance content is negatively affected by a coarse excipient as proposed in DE-A-1792207. The term "inhalable" means those particles which are transported deep into the branches of the lungs when inhaled with the inspired air. The particle size required for this is less than 10 μm, preferably less than 6 μm. Flowability, expelability and dispersibility of the powder are also of major importance in other types of inhalation equipment, eg. those which measure out each individual dose from a supply by means of a measuring chamber, (eg. as described in U.S. Pat. No. 4,570,630) or contain the individual dose in recesses provided in a circular disk (eg. as described in DE-A-3625685).

It has now been found that the inhalable portion of the active substance of inhalable powders can be controlled, within wide limits, whilst at the same time retaining the good accuracy of metering, if the active substance micronised into inhalable particles is combined with suitable quantities of a mixture of one or more physiologically acceptable excipients, one component of the excipient mixture having a mean particle size of less than about 10 μm and the other having a mean particle size greater than about 20 μm, the average particle size generally being below 150 μm and preferably less than 80 μm.

The weight ratios of fine and coarser excipient are between 1:99 and 95:5, preferably between 5:95 and 70:30, especially between 10:90 and 50:50.

Since the individual dose of most pharmaceutical preparations administered by inhalation is small, the proportion thereof in the mixture is usually very small, eg. 0.01 to 0.1 mg of active substance to about 5 mg of excipient mixture. The quantity of preparation administered on each inhalation may be selected within wide limits. So as to avoid administering excessive amounts of excipient to the patient, the skilled person will endeavour to minimise the quantity inhaled. On the other hand, extremely small amounts are difficult to handle and measure out. Accordingly, the quantity of preparation for each application will be between about 1 and 20, preferably between 2 and 10 mg. Having said that, however, it is not fundamentally out of the question to go above or below the values specified.

As explained hereinbefore, generally the active substances administered by inhalation are so potent that the quantity thereof does not significantly help to determine the size of the quantity of preparation. Rather, the pharmacist is able to control the quantity of active substance delivered by inhalation by varying the quantities of excipient and the range of particle sizes. This may be necessary, for example, if the same effect is to be achieved as with a preparation which has already been clinically tested or is on sale.

Finely divided and coarser excipients may consist of chemically identical or chemically different substances. The excipient mixtures may, for example, contain one chemical substance as the fine excipient and a different substance as the coarser excipient. However, the fine and coarser excipients in question may also themselves constitute mixtures of different substances. Apart from the active substances and excipients mentioned above, the preparations according to the invention may contain minor amounts of other additives eg. flavour correctors.

Pharmaceutically suitable and physiologically harmless excipients for inhalation purposes are known. Examples include monosaccharides (such as glucose and arabinose); disaccharides (such as lactose, saccharose and maltose); polysaccharides (such as dextrans); polyalcohols (such as sorbitol, mannitol and xylitol); salts (such as sodium chloride and calcium carbonate) or mixtures of these excipients with one another. Lactose and glucose are preferred.

The examples which follow show how different proportions of excipients affect the proportion of active substance which can be delivered by inhalation. Glucose with an average particle size of 35 μm (G I) and of 5 μm (G II) or 8 μm (GIII) was used as excipient. The mixture of excipients with the active substance was packaged, in 5 mg portions, into conventional capsules for powder inhalation and delivered from these capsules using an apparatus according to DE-A-3345722.

In Example 1 the mixture contains, per capsule, 0.1 mg of fenoterol of an average particle size of <6 μm and in Example 2, 0.04 mg of ipratropium bromide with an average particle size of <6 μm.

"W" is the proportion of active substance delivered by inhalation as a percentage of the quantity contained in the mixture.

| | Example 1 | |
|---|---|---|
| G I (%) | G II (%) | W (%) |
| 100 | 0 | 14.4 |
| 96 | 4 | 21.7 |
| 84 | 16 | 31.0 |

| | Example 2 | |
|---|---|---|
| G I (%) | G III (%) | W (%) |
| 100 | 0 | 15.1 |
| 95 | 5 | 15.7 |
| 90 | 10 | 23.0 |
| 75 | 25 | 33.4 |
| 50 | 50 | 38.3 |

We claim:

1. Powder for inhalation comprising a micronized active substance and a physiologically acceptable excipient comprising a mixture containing a fine fraction having an average particle size in the range of less than 10 μm and a coarse fraction having an average particle size in the range of from about 20 μm to about 150 μm, wherein the weight ratio of micronized active substance to the physiologically acceptable excipient mixture is from about 0.01:5 to 0.1:5.

2. Powder for inhalation according to claim 1 characterized in that the weight ratio of the fine fraction to the coarse fraction in the physiologically acceptable excipient mixture is between 1:99 and 95:5.

3. Powder for inhalation according to claim 1 or 2 characterized in that the fine fraction and the coarse fraction in the physiologically acceptable excipient mixture are each individually selected from the group consisting of monosaccharides, disaccharide's, polysaccharides, polyalcohols and inorganic salts.

4. Powder for inhalation according to claim 3 characterized in that the fine fraction and the coarse fraction in the physiologically acceptable excipient mixture consists of the same chemical substance.

5. Powder for inhalation according to claim 3 characterized in that the fine fraction and the coarse fraction in the physiologically acceptable excipient mixture consists of a different chemical substance.

6. Powder for inhalation according to claims 1 or 2 characterized in that the weight ratio of the fine fraction to the coarse fraction in the physiologically acceptable excipient mixture is between 5:95 and 70:30.

7. Powder for inhalation according to claim 6 characterized in that the weight ratio of the fine fraction to the coarse fraction in the physiologically acceptable excipient mixture is between 10:90 and 50:50.

8. Powder for inhalation according to claim 7 characterized in that the coarse fraction has an average particle size in the range of from about 20 μm to about 8 μm.

* * * * *